United States Patent [19]

Larsen et al.

[11] Patent Number: 4,981,956

[45] Date of Patent: Jan. 1, 1991

[54] DNA SEQUENCES ENCODING BOVINE GROWTH FACTORS

[75] Inventors: Brent R. Larsen, St. Charles, Mo.; Ned R. Siegel, Belleville, Ill.; Claire E. Kotts, St. Louis, Mo.; Michael F. McGrath, Chesterfield, Mo.; Sharon D. Ogden, St. Louis, Mo.; Gwen G. Krivi, Olivette, Mo.; John C. Minnerly, Creve Coeur, Mo.

[73] Assignee: Monsanto Company, St. Louis, Mo.

[21] Appl. No.: 254,332

[22] Filed: Oct. 6, 1988

Related U.S. Application Data

[60] Division of Ser. No. 888,996, Jul. 31, 1986, Pat. No. 4,783,524, which is a continuation-in-part of Ser. No. 777,117, Sep. 17, 1985, abandoned.

[51] Int. Cl.$^5$ .................. C07H 21/00; C07H 21/04

[52] U.S. Cl. ........................... 536/27; 536/28; 536/29

[58] Field of Search ............... 536/27, 28, 29

*Primary Examiner*—John W. Rollins
*Assistant Examiner*—L. Eric Crane
*Attorney, Agent, or Firm*—Carol H. Clayman; George R. Beck; Jon H. Beusen

[57] ABSTRACT

This invention relates to novel peptides having utility for promotion of growth and/or lactation in animals, to processes and DNA useful in production of such peptides, and to methods utilizing such peptides to promote growth or lactation in animals. In some embodiments, the invention is directed to peptides having bovine IGF-II biological activity, to production of such peptides, and to their use in effecting proliferation of certain cells (e.g. mammary epithelial or muscle) or in enhancing lactation in cattle or other animals.

9 Claims, No Drawings

DNA SEQUENCES ENCODING BOVINE GROWTH FACTORS

CROSS-REFERENCE TO RELATED APPLICATION

This is a divisional of Application Ser. No. 888,996 filed July 31, 1986 and now U.S. Pat. No. 4,783,524 issued Nov. 8, 1988, which was a continuation-in-part of application Ser. No. 777,117 filed Sept. 17, 1985, now abandoned.

BACKGROUND OF THE INVENTION

Insulin-like growth factors (IGF's) have been identified in various animal species as peptides that are biologically active in growth, e.g. via proliferation of cells. They are believed to mediate effects of somatotropins and possibly other hormones. The designation "insulin-like growth factor" was chosen to express the insulin-like structures and effects of these peptides. IGF's have nearly 50% homology with insulin. In three dimensional structure they resemble proinsulin, i.e., they are single-chain peptides cross-linked by three disulfide bridges and containing an A-chain portion (A domain), a B-chain amino-terminal portion (B domain) and an A-B connecting chain (C domain). A carboxy-terminal extension (D domain) not found in proinsulin is also present in at least some IGF's.

Several classes of IGF's have been identified in animals. Normally these include IGF-I, IGF-II and others. Circulating levels of these peptides appear to be under the control of somatotropin to some extent, with IGF-I controlled to a greater extent than IGF-II. In various cell culture systems, IGF's have shown mitogenic effects measured, e.g., by increased tritiated thymidine incorporation.

It has been demonstrated that in some animals, at least two sets of IGF receptors exist, one preferentially binding IGF-I and the second IGF-II, suggesting separate functions for IGF-1 and IGF-II. However, the biological functions of IGF-II appear to vary among mammalian species. For example, while rat IGF-II levels have been found 20-100 fold higher in fetal than maternal circulation, human serum IGF-II in the fetus is normally lower than in adults.

Because of its potential bioactivity and utility for enhancing desirable cell growth in animals, the amino acid sequence of bovine IGF-II ("bIGF-II") has long been sought together with a more detailed understanding of its growth-promoting and other activities, its active fragments, etc. Heretofore, neither that sequence nor the DNA sequence of the bIGF-II gene has been reported.

Studies with rat and human genomic libraries suggest that IGF-II genes contain at least four exons. The large size and complexity of the genes for human and rat IGF-II have made their isolation and identification so difficult that the DNA sequences of those genes have not yet been fully determined. For purposes of making and studying bIGF-II, however, there has been a need to isolate and determine the complete DNA sequence of the bIGF-II gene.

Accordingly, it is an object of this invention to provide highly purified and/or synthetic peptides having one or more of the biological activities of bIGF-II and, more generally, such peptides consisting essentially of amino acids providing such activity, or peptides which can be readily converted to those having such activity.

It is another object of this invention to provide methods using such peptides to promote desirable growth or functionality of cells in animals including, e.g., muscle and/or mammary epithelial cells.

Another object of this invention is to provide DNA useful in making such peptides.

Another object of this invention is to provide processes utilizing such DNA in the production of such peptides.

Other objects will be apparent from the detailed description herein and the appended claims.

SUMMARY OF THE INVENTION

This invention is based largely on the herein-reported original discoveries of the amino acid sequences of bIGF-II and various precursors thereof, and the nucleotide sequences of DNA coding for bIGF-II and such precursors, all as shown hereinbelow.

In one embodiment, the invention provides certain novel peptides consisting essentially of the following sequence of amino acids (reading from the amino end to the carboxy end of said sequence) which correspond to the heretofore-undetermined amino acid sequence of bIGF-II:

Ala—Tyr—Arg—Pro—Ser—Glu—Thr—Leu—Cys—Gly—
Gly—Glu—Leu—Val—Asp—Thr—Leu—Gln—Phe—Val—
Cys—Gly—Asp—Arg—Gly—Phe—Tyr—Phe—Ser—Arg—
Pro—Ser—Ser—Arg—Ile—Asn—Arg—Arg—Ser—Arg—
Gly—Ile—Val—Glu—Glu—Cys—Cys—Phe—Arg—Ser—
Cys—Asp—Leu—Ala—Leu—Leu—Glu—Thr—Tyr—Cys—
Ala—Thr—Pro—Ala—Lys—Ser—Glu.

In other embodiments, the invention provides various methods for promoting growth and/or other desirable functions of cells in animals by administering peptides of this invention to animals in amounts sufficient to cause such effects. For example, animal muscle mass can be increased by suitably administering to the animal an amount of such peptide(s) effective to cause proliferation of satellite muscle cells in that animal. In another illustration, such peptide(s) can be suitably administered to female mammals in amounts effective to cause proliferation and/or galactopoietic stimulation of their mammary epithelial cells such that subsequent lactation is enhanced.

In other embodiments, the invention provides certain novel nucleotide sequences (DNA) coding for such peptides. Typically, this DNA contains essentially the following sequence of nucleotides (or their functional equivalents for peptide expression):

5'-GCT TAC CGC CCC AGC GAG ACT CTG TGC GGC
GGG GAG CTG GTG GAC ACC CTC CAG TTT GTC
TGT GGG GAC CGC GGC TTC TAC TTC AGC CGA
CCA TCC AGC CGC ATA AAC CGA CGC AGC CGT
GGC ATC GTG GAA GAG TGT TGC TTC CGA AGC
TGC GAC CTG GCC CTG CTG GAG ACT TAC TGT
GCC ACC CCC GCC AAG TCC GAG-3'.

In other embodiments, the invention provides processes for producing such peptides by effecting expression of such DNA, recovering and then optionally further purifying the resulting peptides, e.g. to an essentially pure form.

DETAILED DESCRIPTION OF THE INVENTION

As used herein, the symbols representing amino acids (e.g. Ala for alanine) and nucleotides (C, A, G or T) are those conventionally employed. See Lehninger (1976).

The Peptides

As used herein, the term "synthetic peptide" means a peptide produced by a technique (e.g. chemical synthesis or recombinant DNA expression) other than its natural production in a living animal. Accordingly, the "synthetic" peptides of this invention are to be distinguished from peptides produced in living animals via expression of DNA occurring naturally in those animals. As produced, such "synthetic" peptides are normally free from peptides of bovine (and usually other animal) origin.

In other embodiments, however, peptides of this invention can be prepared by isolation from peptide mixtures produced in living animals, e.g. as in Example 1. Using any mode of preparation in which a peptide of this invention is isolated from other peptide(s) of bovine or other animal origin, the isolation is typically carried out to provide a peptide of this invention essentially free from such other peptide(s), i.e., mixed with little enough of such other peptide(s) that the latter do not interfere substantially with the desired bioactivity of the peptide of this invention.

As used herein, references to peptides "consisting essentially" of the sequence of bIGF-II (alone or extended at either or both of its amino and carboxy termini) should be understood as referring to peptides comprising the recited sequence or only as much of that sequence as is needed to provide one or more of the biological activities of bIGF-II in substantial measure (typically at least about 0.1%, preferably at least about 1% and even more desirably at least about 10% of that activity of pure intact bIGF-II). Those biological activities of bIGF-II include, but are not limited to, insulin-like activity and the ability (alone or with other biologically active substances) to stimulate animal cell proliferation or lactation by already-formed mammary epithelial cells. Amino acids that are essentially superfluous with respect to such activity can be omitted, resulting in peptides of fewer amino acids than are contained in the recited peptide itself. Also embraced by such references are peptides which have such activity despite the presence therein of one or more amino acids substituted for any of those in the amino acid sequences (shown herein) of bIGF-II or its naturally-occurring precursors. For example, peptides in which a methionine is substituted for the amino-terminal alanine in the bIGF-II sequence shown above is expected to have bIGF-II-like activity and to be readily producible via recombinant DNA (rDNA) in bacteria or other microorganisms that do not remove such an N-terminal methionine residue. Also embraced by such references are various larger peptides containing the recited sequence (or such a deletion and/or substitution variant thereof) together with one or more additional amino acids directly attached to its amino and/or carboxy terminus, as well as such peptides otherwise modified at their termini or elsewhere, e.g. by glycosylation, phosphorylation, amidation or the like, to the extent such peptides can be used (with or without further processing) to provide a biological activity of bIGF-II in substantial measure.

In one approach employed in identifying the bIGF-II amino acid sequence disclosed herein, bIGF-II was isolated and purified from bovine serum. Although the liver is the major source of IGF production in most animals, and IGF's have been detected in many body tissues such as muscle, cartilage, brain and cerebral spinal fluid, serum is the preferred source of IGF's generally, and IGF-II specifically. Methods for separation and isolation of IGF's have been described in the art, e.g. by Svoboda et al., Van Wyk et al., Liberti, Bala et al. and Zumstein et al.

The active bIGF-II isolated and purified from bovine serum in accordance with the present invention was found to be a single peptide having a molecular weight of about 7400 daltons and the sequence of 67 amino acids shown above. A preliminary screen for biological activity associated with the purified bIGF-II and quantitation thereof was performed by a rat placenta radioreceptor assay described in Daughaday et al.

The present discovery of the complete amino acid sequence of bIGF-II is significant as it provides a basis for production of peptides having bIGF-II activity. Such production can be carried out by any available process. For example, small (e.g. research) quantities can be produced using conventional peptide synthesizing equipment. On a larger scale, such production can be carried out by chemical synthesis or, usually more satisfactorily, in microbial hosts or cell cultures utilizing rDNA coding for peptides of this invention. Using such DNA in conjunction with techniques of genetic engineering, there can be manufactured much larger quantities of such peptides than could ever be practically recovered from bovine serum or tissues.

As described more fully below, the amino acid sequence of bIGF-II has now been confirmed by isolating and characterizing bIGF-II gene fragments from bovine kidney genomic DNA. Even before such gene characterization, however, synthetic peptides of this invention simulating bIGF-II structurally could be produced following the herein-reported discovery of the bIGF-II amino acid sequence, e.g. by known techniques using rDNA made to code for that amino acid sequence. Thus, when such peptides are to be produced using rDNA in microbial hosts such as bacteria or yeast, a DNA sequence coding for that amino acid sequence and optionally composed of bIGF-II codons preferred by the selected host (see U.S. Pat. No. 4,356,270 issued Oct. 26, 1982 to K. Itakura) can be designed and produced synthetically.

Production of peptides of this invention by rDNA and/or chemical synthesis may result in minor alterations in amino acid composition. For example, production in bacteria may result in addition of a methionine at the amino (N-) terminus, chemical synthesis may result in variations of the carboxy (C—) terminus such that any of the radicals —COOR:, —CR$_1$O, —CONHNR, —CONR$_1$R$_2$ or —CH$_2$OR (R$_1$ and R$_2$ being independently lower alkyl or hydrogen) may be found. These peptides are among those of the present invention insofar as their bIGF-II-like biological activity is not diminished to an intolerable degree.

In some instances, peptides of this invention will be isolated or prepared in a denatured, biologically inactive condition. In its normal, biologically-active (undenatured) state, bIGF-II is cross-linked by three disulfide bridges. By analogy to human IGF-II and IGF-1, these bridges are believed to exist between amino acid (cysteine) positions 9 and 47, 21 and 60, and 46 and 51 (see Yamashiro et al.), but the scope of this invention is not to be limited thereto. Peptides of this invention that lack such desired bridging can be activated by peptide naturation techniques well known in the art, usually by subjecting the peptide to conditions (pH, temperature, oxidizing environment, etc.) under which it assumes its biologically active, three-dimensional configuration and forms the disulfide bonds (bridges) similar to those in biologically active bIGF-II. The particular technique employed is not critical for purposes of this invention so long as biological activity is conferred to the extent desired.

The amino acid sequence differences between human, rat and bovine IGF-II's occur mainly in the regions generally characterized as their C domains. bIGF-II analyzed for purposes of the present invention was consistently found to have an N-terminal alanine as shown in TABLE II. This was consistent with the N-terminal alanine reported for human and rat bIGF-II's by Humbel but at variance with the N-terminal tyrosine (des Ala) reported for human IGF-II in Rinderknecht et al. and rat IGF-II in Marquardt et al. Such bIGF-II's having an N-terminal tyrosine may exist as a result of allelic and/or processing variations not detectable from the bovine serum used herein, or as a consequence of unintended deletion of the N-terminal alanine during purification. In any event, such N-tyrosine variants are to be considered equivalents of the peptides of this invention to the extent they have bIGF-11 biological activity.

With the herein-reported amino acid sequence and biological activities of bIGF-II, it is now possible to identify allelic forms of bIGF-II and/or make bIGF-II variants having biological activities equal or superior to those of bIGF-II. Hence it is anticipated that the isolation of allelic forms of bIGF-II and production of such variants having amino acid deletion(s), substitution(s) and/or addition(s) with respect to bIGF-11 will provide various useful embodiments of the peptides disclosed herein. Identifying such alternative peptides is within the ability of those skilled in the art.

From DNA sequencing described below, and by analogy to human IGF-II ("hIGF-II"), it is believed that bIGF-II is first synthesized intracellularly as a precursor peptide having a signal (leader) sequence of at least 24 amino acids immediately preceding the N-terminus of the mature bIGF-II and that, on secretion of the precursor peptide from bIGF-II-producing cells, that signal sequence is cleaved. The peptides of this invention containing such a signal sequence (or any desired portion thereof) can be produced by expression of such DNA (first deleting the codon(s) for any amino acid(s) not wanted in that sequence) and are useful for production of peptides of this invention corresponding in amino acid sequence to mature bIGF-II, e.g. via chemical, microbial or enzymatic removal of that signal sequence.

From other novel DNA sequences disclosed herein, it is believed that there is a bIGF-II precursor peptide having a carboxy-terminus extension containing about 89 amino acids. The novel sequence of the first 68 amino acids of that extension (beginning at the carboxy terminus of bIGF-11) is disclosed herein. By analogy to pro-insulin, it is believed that peptides of this invention containing such a carboxy extension provide the biological activity of bIGF-II in substantial measure and accordingly, these extended peptides are within the scope of the present invention.

Uses of the Peptides

As described more fully below, the isolation and characterization of bIGF-II in accordance with the present invention has provided an opportunity to more clearly identify and define aspects of the bioactivity of bIGF-II. For example, it has been found that bIGF-II is active in the rat L6 myoblast cell proliferation assay and is able to stimulate proliferation of bovine mammary epithelial cells and lactation by such mammary cells in vitro. Accordingly, it is considered that the peptides of this invention have activity for in vivo proliferation of various bovine cells, e.g. mammary epithelial and satellite muscle cells, and for in vivo stimulation of already-formed mammary epithelial cells to increase their rate of milk production. It is further considered that peptides of the present invention are effective for similarly increasing the muscle content and/or lean-to-fat ratio in animal species other than cattle (e.g. sheep, goats, swine, chickens, turkeys, ducks and other fowl) and for increasing lactation in mammals other than cattle (e.g. sheep, goats and swine) when sufficient homology exists between bIGF-II and the IGF-II's of such animal species.

In adult animals, the myofiber (e.g. muscle cell) number is fixed so that increased muscling results only from muscle cell hypertrophy and proliferation of satellite muscle cells. Myofibers are formed in utero by the fusion of replicated embryonic muscle cells. Replicating muscle cells which persist in the adult are called satellite muscle cells. Satellite muscle cells may be stimulated to replicate and thereafter fuse with existing myofibers to yield increased myofiber nuclei. This increase in myofiber nuclei is expected to manifest itself as increased muscle content (mass).

The L6 myoblast proliferation assay provides a reliable in vitro indicator of IGF activity and is used as a model for factors affecting embryonic myoblasts and adult satellite cells. Factors active in this system behave similarly in primary cultures of bovine myoblasts. See Gospodarowicz et al. The enhancement of rat L6 myoblast proliferation in vitro by a peptide of this invention indicates its activity in causing increased myoblast proliferation and, therefore, an increase in ultimate myofiber number in utero. In addition, similar enhancement of rat L6 myoblast proliferation indicates that peptides of this invention can be used to enhance adult muscle hypertrophy, e.g. via stimulation of satellite muscle cell proliferation.

In lactating animals, the amount of mammary epithelial tissue is a limiting factor in milk production, as these are the cells which produce and secrete milk. Employing in vitro systems, it has been demonstrated that epithelial cells obtained from mammary glands of animals can be stimulated by bIGF-II to proliferate to produce increased quantities of milk constituents. It has further been demonstrated that mammary epithelial cells stimulated to proliferate in one such in vitro cell system can be reimplanted in cleared mammary fat pads (see Yang and Nandi) where they can be stimulated to proliferate and/or produce milk. These discoveries indicate that peptides of this invention are biologically active in vivo for increasing bovine lactation, e.g. by any suitable administration to pregnant cows or heifers. One such technique is described in copending U.S. Pat. application Ser. No. 837,477 filed Mar. 7, 1986, the disclosure of which is incorporated herein by reference.

Thus, the peptides of this invention are useful for administration to animals, especially (but not only) non-human animals, for increasing milk production and/or the lean-to-fat ratio or muscle content in animals. For purposes of such uses, one or more peptides of this invention (or non-toxic salts thereof) can be combined with a non-toxic, physiologically acceptable carrier (liquid or solid) to form a composition which can be administered to animals by any suitable technique, e.g. intravenously, subcutaneously, intramuscularly, intranasally, or orally in a form that protects the peptide from degradation in the digestive tract. Such compositions can be administered to the animal by injection, infusion or implantation, preferably in a medium (e.g. dispersion in oil or a polymer) which facilitates delivery of the peptide to target cells of the animal at a desired rate. The proportions of carrier and biologically active peptide in such compositions can be any that facilitate the desired effects in animals. Preferred proportions can be readily determined by those skilled in the art.

The required dosage will vary with the particular result sought and duration of desired treatment. The amount or dosage most effective for achieving a desired result (e.g. increased milk production) can be determined by routine experimentation. The preferred dosage may depend on such variables as the size, general health and nutritional status of the specific animal.

Bioactive peptides of this invention can be used in an essentially pure form, i.e., free from other peptides (of whatever origin) having a significant effect on the bioactivity of the peptide(s) of this invention. This is not essential, however, as in many utilities peptides of this invention can be used satisfactorily (in many cases, even advantageously) in mixtures or other combinations with different peptides, e.g. other animal growth factors such as bovine (or other animal) IGF-I, EGF or TGF-α (alpha-transforming growth factor).

The DNA

As used herein with reference to such DNA, the term "synthetic" means it has been made by any technique other than its natural replication in a living animal. Utilizing the nucleotide sequences described herein, any DNA of this invention can be prepared by various techniques well known in the art, e.g. automated DNA synthesizing equipment, other chemical synthesis procedures, cDNA or cloning in a microorganism. Any suitable technique can be used.

As used herein, the term "containing a] sequence of nucleotides" means that the recited nucleotides are present in such DNA without intervening non-translated nucleotides (e.g. introns). Since the naturally-occurring DNA for bIGF-II contains such intervening untranslated nucleotides, the DNA of this invention containing nucleotide sequences lacking any of such untranslated nucleotides are ipso facto "synthetic."

The term "essentially pure", when used herein to describe nucleic acid (DNA or RNA) sequences or molecules, means substantially free from nucleic acid sequences with which the described sequence or molecule is normally associated in its natural state.

For purposes of this invention, DNA fragments coding for the mature bIGF-II peptide, a precursor including a leader sequence containing 24 amino acids, and 68 of 89 amino acids of a carboxy extension (E domain) have been isolated and sequenced. As described in Example 4, essentially pure DNA fragments coding for these peptides were isolated from bovine kidney genomic DNA. Analysis of these fragments revealed the following DNA sequence and corresponding amino acid sequence for a bIGF-II precursor protein:

NH₂—

—Met—Gly—Ile—Pro—Met—Gly—Lys—Ser—Met—Leu—
5'-ATG GGA ATC CCA ATG GGG AAG TCG ATG CTG

Val—Leu—Leu—Thr—Phe—Leu—Ala—Phe—Ala—Ser—
GTG CTT CTC ACC TTC CTT GCC TTC GCC TCG

Cys—Cys—Ile—Ala—Ala—Tyr—Arg—Pro—Ser—Glu—
TGC TGC ATT GCT GCT TAC CGC CCC AGC GAG

Thr—Leu—Cys—Gly—Gly—Glu—Leu—Val—Asp—Thr—
ACT CTG TGC GGC GGG GAG CTG GTG GAC ACC

Leu—Gln—Phe—Val—Cys—Gly—Asp—Arg—Gly—Phe—
CTC CAG TTT GTC TGT GGG GAC CGC GGC TTC

Tyr—Phe—Ser—Arg—Pro—Ser—Ser—Arg—Ile—Asn—
TAC TTC AGC CGA CCA TCC AGC CGC ATA AAC

Arg—Arg—Ser—Arg—Gly—Ile—Val—Glu—Glu—Cys—
CGA CGC AGC CGT GGC ATC GTG GAA GAG TGT

Cys—Phe—Arg—Ser—Cys—Asp—Leu—Ala—Leu—Leu—
TGC TTC CGA AGC TGC GAC CTG GCC CTG CTG

Glu—Thr—Tyr—Cys—Ala—Thr—Pro—Ala—Lys—Ser—
GAG ACT TAC TGT GCC ACC CCC GCC AAG TCC

Glu—COOH
GAG-3'

The foregoing underlined DNA sequence and corresponding amino acid sequence are those of mature bIGF-II as identified for purposes of the present invention. As shown in the above bIGF-II precursor peptide sequence, three possible translation start-signal codons (ATG's) are in-frame with the DNA sequence coding for mature bIGF-II. It is believed that the first of those ATG's constitutes the operable start of translation for the bIGF-II precursor, but certain host cells may recognize one of the alternative in-frame translation start-signal codons, thereby giving rise to a bIGF-II precursor having an alternative (shorter) leader sequence. If desired, such shortened precursor peptides can be produced by other means, e.g. by using synthetic DNA of this invention beginning with one of the alternative ATG translation start-signal codons.

Further, the gene fragments isolated and sequenced in the present invention revealed an E domain (carboxy-terminal extension) for another precursor of the mature bIGF-II peptide. This extension and the DNA coding for it were found to have the following sequences:

NH₂—

—Arg—Asp—Val—Ser—Ala—Ser—Thr—Thr—Val—Leu—
5'-AGG GAT GTC TCT GCC TCT ACG ACC GTG CTT

Pro—Asp—Asp—Val—Thr—Ala—Tyr—Pro—Val—Gly—
CCG GAC GAC GTC ACC GCA TAC CCC GTG GGC

Lys—Phe—Phe—Gln—Tyr—Asp—Ile—Trp—Lys—Gln—
AAG TTC TTC CAA TAT GAC ATC TGG AAG CAG

-continued

Ser—Thr—Gln—Arg—Leu—Arg—Arg—Gly—Leu—Pro—
TCC ACC CAG GGC CTG CGG AGG GGC CTG CCC

Ala—Phe—Leu—Arg—Ala—Arg—Arg—Gly—Arg—Thr—
GCC TTC CTG CGA GCA CGC CGG GGT CGC ACG

Leu—Ala—Lys—Glu—Leu—Glu—Ala—Leu—Arg—Glu—
CTC GCC AAG GAG CTG GAC GCG CTC AGA GAG

Ala—Lys—Ser—His—His—Pro—Leu—Ile—COOH
GCC AAG AGT CAC CAT CCG CTG ATC-3'.

The discovery and isolation of the DNA sequence for bIGF-II are significant as they not only verified the amino acid sequence determined for purified bIGF-II but provided the DNA sequences and corresponding amino acid sequences for the bIGF-II leader peptide, and carboxy-terminal peptide extension (E domain). Further, the novel DNA sequences of this invention enable those skilled in the art to identify, isolate and/or provide other bIGF-II precursor proteins and/or biologically active fragments thereof including, but not limited to, other peptides having bIGF-II-like activity. The biological activities of these peptides, fragments thereof and products containing same can include, but are not limited to, the growth- and/or lactation-promoting activities of bIGF-II described herein, and can be ascertained in accordance with herein-described or other in vitro and/or in vivo assays. These biologically active fragments and products are herein referred to as "IGF-II gene-related proteins" and include peptides at least a portion of which is encoded in DNA of this invention, allelic variations thereof and/or DNA that hybridizes to DNA of this invention. Having been derived using DNA of this invention or such variations, those IGF-II gene-related proteins are within the scope of this invention.

The DNA sequences and genes of the present invention now enable those skilled in the art to more effectively study and/or control IGF-II biosynthesis and biological regulations. Additionally, DNA sequences of this invention can be employed by those skilled in the art to identify and isolate other IGF DNA sequences, IGF genes and IGF gene-related peptides in other species such as, but not limited to, ovine, caprine porcine and avian IGF's, wherein sufficient DNA sequence and/or peptide homology exists.

The discovery of the aforementioned leader (signal) sequence enables construction of DNA vectors for production of bIGF-II-like peptides in eucaryotic cells (e.g. mammalian cells and yeast) capable of recognizing and removing the signal sequence, or bIGF-II precursor peptides containing the signal peptide and/or E domain in procaryotic hosts such as bacteria.

A preferred method for producing the synthetic peptides of the present invention is by rDNA technology utilizing host cells such as bacteria (e.g. E. coli) or eucaryotic cells such as yeast. Modifications of these DNA sequences herein can be made to affect their efficiency of peptide production in a desired host cell. Such modifications include, but are not limited to, host-preferred codon substitution, construction of DNA coding for fusion proteins including a peptide of this invention, substitution of codons to eliminate or enhance mRNA structural features affecting their translation, and other modifications that improve production of such peptides in the selected host cell. The peptides so produced which exhibit biological activity of the purified bIGF-II described herein in substantial measure are to be considered equivalents of the peptides of this invention.

The following examples illustrate specific embodiments of the invention. They are not to be taken as limiting the invention's scope in any way. Various modifications will be apparent to those skilled in the art, with or without the other disclosure herein. All temperatures are in degrees Celsius unless otherwise stated.

EXAMPLE I

As described in this example, the complete amino acid (AA) composition and sequence of bIGF-II were determined from that peptide isolated and purified from adult bovine serum obtained from Sigma Chemical Co. (St. Louis, Mo.).

Partially purified fractions of such bIGF-II were obtained using a combination of isolation procedures described by Svoboda et al. and Zumstein et al. The complete purification of bIGF-II essentially free from other bovine peptides was achieved by reverse phase high performance liquid chromatography (HPLC). All HPLC procedures were accomplished using trifluoroacetic acid (TFA) and acetonitrile. The solvents were delivered to the column at 2 ml/min using a Perkin-Elmer (Norwalk, Conn.) Series 4 HPLC pumping system, and the peptide was visualized using a Hewlett Packard (Greenly, Conn.) 1040A UV/VIS detector. All chromatographic procedures were carried out at ambient room temperatures (23°–28°).

The bIGF-II used for the initial sequence determination was prepared using a Chromega fluorodecyl 4.1×250 mm column (E.S. Industries, Marlton, N.J.). Elution of bIGF-II from the Chromega column was accomplished using a linear gradient of acetonitrile from 15–50% (v/v) over 35 min with the TFA concentration maintained at 40 mM. The bIGF-II samples used for complete structural verification were prepared using a Nucleosil C-18 4.1×250 mm column (Altech Associated, Deerfield, Ill.). The solvent system employed for separation on the column was a linear acetonitrile gradient from 30–35% (v/v) over 15 minutes with a constant TFA concentration of 20 mM. Identification of the active bIGF-II was made using the rat placenta radioreceptor assay described in Daughaday et al. This assay also provided an estimate of the quantity of bIGF-II in the final samples.

The HPLC-purified bIGF-II was subjected to AA sequence analysis using an Applied Biosystems, Inc. (Foster City, Calif.) Protein Sequencer Model 470A according to the methods described by Hunkapiller et al. (1983a and b). Briefly, 2.5 nanomoles of the HPLC-purified bIGF-II were lyophilized and analyzed on that Sequencer employing an Edman degradation reaction consisting of derivatizing the N-terminal AA with a reagent followed by cleavage of that AA and ultimate release as its phenylthiohydantoin (PTH) derivative.

Since N-terminal sequence analysis was unable to provide the complete structure for the peptide, the purified IGF-II was derivatized and enzymatically hydrolyzed using the following procedure: After purification, 75 mg bIGF-II was subjected to performic acid oxidation using the procedure of Hirs for denaturation by converting sulfhydryls to cysteic acid residues. The peptide was dissolved in 50 ml 88% formic acid (Fisher Scientific, Springfield, N.J.) and the solution cooled to 0°. After one hour at room temperature, 5 ml of the performic acid reagent (0.5 ml 30% H$_2$O$_2$ (Fisher Scientific) in 9.5 ml 88% formic acid) was added to the peptide solution. The resulting mixture was allowed to stand at 10° while progress of the reaction was followed using the second reverse phase HPLC procedure specified. On completion (after 45 min), 4 ml water was added to the mixture and the reagents were removed in vacuo using a Speed Vac Concentrator (Savant Instruments, Farmingdale, N.Y.).

The residue remaining after solvent removal was dissolved in 1 M NaHCO$_3$ containing 1 mM CaCl$_2$ (both Fisher Scientific). The enzymatic hydrolysis was initiated by adding 2 ml of a 0.1 M HCl/2 mM CaCl$_2$ solution containing 8 mg/ml alpha-chymotrypsin (Sigma Chemical Co.) (16 mg protein added). After 45 min at room temperature, the chymotrypsin was removed using a Centricon-10 (Amicon Corp., Danvers, MA) ultrafiltration device. The filtrate (O-IGF-II chymotryptic hydrolysate) was subjected to reverse phase chromatography using the Nucleosil column and the 20 mM TFA/acetonitrile solvent previously specified. Eluting the column with a linear gradient of acetonitrile from 10 to 70 % (v/v) over 30 min resolved the hydrolysate into 10 major peptide-containing peaks. Sequence analysis of the peptides (performed as above on Model 470A Sequencer in conjunction with an Applied Biosystems Inc. Model 120A PTH Analyzer) from 3 isolated peaks showed that 2 of them contained the AA's required to complete the primary structure elucidation for bIGF-II.

TABLE II shows the N-terminal sequence analysis of the peak HPLC material together with the published sequences for human and rat IGF-II's. Residues 1–43 of the bIGF-II were determined by N-terminal sequence analysis of the purified bIGF-II. Residues 37–59 and 60–67 were determined by N-terminal sequence analysis of the two separate chymotryptic fragments. Molar cysteic acid content of the peptides was verified using precolumn orthophthalaldehyde AA analysis as described in Larsen et al. As shown in TABLE II, three differences were found between the bovine and human sequences and three differences were found between the bovine and rat sequences.

TABLE II

IGF-II Amino Acid Sequences

Bovine  NH$_2$—Ala—Tyr—Arg—Pro—Ser—Glu—Thr—Leu—Cys—Gly—Gly—Glu—Leu—Val—Asp—Thr—Leu—Gln—Phe—

Human  NH$_2$—Ala—Tyr—Arg—Pro—Ser—Glu—Thr—Leu—Cys—Gly—Gly—Glu—Leu—Val—Asp—Thr—Leu—Gln—Phe—

Rat  NH$_2$—Ala—Tyr—Arg—Pro—Ser—Glu—Thr—Leu—Cys—Gly—Gly—Glu—Leu—Val—Asp—Thr—Leu—Gln—Phe—

Bovine  Val—Cys—<u>Gly</u>—Asp—Arg—Gly—Phe—Tyr—Phe—Ser—Arg—Pro—Ser—<u>Ser</u>\*  —Arg—<u>Ile</u>\*—Asn—Arg—Arg—

Human  Val—Cys—Gly—Asp—Arg—Gly—Phe—Tyr—Phe—Ser—Arg—Pro—Ala—Ser  —Arg—Val—Ser—Arg—Arg—

Rat  Val—Cys—Ser—Asp—Arg—Gly—Phe—Tyr—Phe—Ser—Arg—Pro—Ser—Gly/Ser  —Arg—Ala—Asn—Arg—Arg—

Bovine  Ser—Arg—Gly—Ile—Val—Glu—Glu—Cys—Cys—Phe—Arg—Ser—Cys—Asp—Leu—Ala—Leu—Leu—Glu—Thr—

Human  Ser—Arg—Gly—Ile—Val—Glu—Glu—Cys—Cys—Phe—Arg—Ser—Cys—Asp—Leu—Ala—Leu—Leu—Glu—Thr—

Rat  Ser—Arg—Gly—Ile—Val—Glu—Glu—Cys—Cys—Phe—Arg—Ser—Cys—Asp—Leu—Ala—Leu—Leu—Glu—Thr—

Bovine  Tyr—Cys—Ala—Thr—Pro—Ala—Lys—Ser—Glu—COOH

Human  Tyr—Cys—Ala—Thr—Pro—Ala—Lys—Ser—Glu—COOH

Rat  Tyr—Cys—Ala—Thr—Pro—Ala—Lys—Ser—Glu—COOH

The bIGF-II residues with an asterisk differ from the corresponding residues in human IGF-II.
The underlined bIGF-II residues differ from the corresponding residues in rat IGF-II.

EXAMPLE II

This example demonstrates the activity of bIGF-II in the rat L6 myoblast proliferation assay. Specifically, the peak HPLC material of Example I was compared to a commercial preparation of human IGF-I from Amgen Inc. (Thousand Oaks, Calif.) for demonstrable physiological activity in that assay.

Rat L6 myoblasts described by Yaffee were used as described by Kotts. All incubations were carried out at 37°, 10% CO$_2$, and 100% humidity. A Coulter Counter (Model ZM) equipped with a C-1000 Channelyzer (Coulter Electronics, Hialeah, FL) was used for cell counting. Stock cultures were maintained in Dulbecco's Minimum Essential Medium (DMEM) (Grand Island Biological Corp. (GIBCO), Grand Island, N.Y.) containing 10% (v/v) fetal calf serum (FCS medium) and routinely plated at 1200 cells/cm$^2$ or 600 cells/cm$^2$ and passaged after 3 or 4 days, respectively, in culture. Passaging was performed by adding 3 ml of 0.05% (w/v) trypsin (GIBCO) in wash buffer (0.8% (w/v) NaCl, 0.04% (w/v) KCl, 0.1% (w/v) dextrose, 0.058% (w/v) NaHCO$_3$, 0.02% (w/v) EDTA, pH 7.4) for 5 minutes at 37° and trypsinization was stopped by adding 7 ml FCS media.

Test cultures were prepared as follows: Stock cultures were trypsinized and pooled and the resulting cell suspension was counted. Based on this count, cells were diluted to the appropriate concentration in FCS media and rapidly plated in 25 cm$^2$ flasks at a density of 600/cm$^2$. 24 hours after plating, the media was removed and cells were rinsed with serum-free DMEM. Test media (4 ml) was then applied to each flask and incubation was carried out for an additional 24 hours after which the culture medium was replaced with fresh test medium. Cultures were then incubated for another 48 hours and counted.

For counting, the test media was removed, cells were rinsed with 2 ml of wash buffer, 1 ml of trypsin solution was added and the cells were incubated for 5 minutes at 37°. The reaction was stopped by addition of 3 ml of cold FCS media. Flasks were pounded 10 times to facilitate cell removal and tipped upright in an ice bath until their contents could be transferred to glass tubes on ice. Each flask was rinsed with 2-3 ml of cold 0.9% (w/v) NaCl and the rinse was added to the cell suspension. Each tube was vortexed gently 5 times to eliminate clumping of cells and the contents of each tube were counted using a Coulter Counter.

Test media for application to the test cultures was prepared by diluting the test sample to the desired concentration with 2% (v/v) FCS medium. The lyophilized peak HPLC material of Example I was dissolved in 30 mM Tris-HCl, pH 7.4 (Tris buffer) to an estimated concentration of 2.6 µM. In Test 1, 0.2 ml of this solution was added to 19.8 ml 2% FCS (26 nM final conc.), filter-sterilized through a 0.22µ filter (Millipore Corp., Bedford, Mass.) and applied to the experimental cultures. A control containing 0.2 ml of the Tris buffer was included for comparison. In Test 2, 0.2 ml of the solution of HPLC material was added to 9.8 ml of 2% (v/v) FCS (estimated 52 nM final conc.), filtered as above, and applied to the experimental cultures. A control containing Tris buffer was prepared similarly.

The positive control for each treatment was $10^{-9}$ M human IGF-I (Amgen Biologicals, Thousand Oaks, Calif.). See Kotts et al. The lyophilized IGF-I was diluted with 44 mM NaHCO$_3$, pH 7.4 to a concentration of 100 pg/ml. A $10^{-8}$ M stock solution was prepared by adding 0.015 ml IGF-1 to 20 ml of 2% (v/v) FCS medium. For $10^{-9}$ M, 2 ml of this stock was added to 18 ml of 2% FCS medium, filter-sterilized and applied to experimental cultures. The control for these cultures was 2% (v/v) FCS medium.

In Test 3, peak HPLC material from Example I was dissolved in 20% acetic acid to an estimated concentration of 165 µM. Two stock media solutions were prepared. A 0.5 µM stock was prepared by adding 0.091 ml of 165 µM solution to 30 ml 2% FCS. pH was adjusted to 7.4 by adding 60 µl of 10% NaOH. A 0.1 µM stock was prepared by adding 0.018 ml of 165 µM solution to 30 ml 2% FCS. pH was then adjusted to 7.4 by adding 10 µl of 10% NaOH. These stock media solutions were filter sterilized and used to prepare serial (1:10 v/v) dilutions. For each serial dilution, 3 ml of the appropriate solution was added to 27 ml 2% FCS. Four controls were prepared. Control A contained 0.091 ml 20% acetic acid in 30 ml 2% FCS; pH was adjusted to 7.4 by adding 60 µl of 10% NaOH. Control B contained 0.018 ml 20% acetic acid in 30 ml 2% FCS; pH was adjusted to 7.4 by adding 10 µl of 10% NaOH. Control C contained 3 ml of Control A and 27 ml 2% FCS. Control D contained 30 ml 2% FCS. Control A was used for the 500 nM bIGF-II test, Control B for the 100 nM bIGF-II test, Control C for the 50 nM bIGF-II test and Control D for the 10 nM, 5 nM, 1 nM, 0.5 nM and 0.1 nM bIGF-II tests.

As shown in TABLE III, bIGF-II significantly stimulated L6 myoblast proliferation at the treatment concentrations tested.

TABLE III

| Treatment | bIGF-II Conc.[a] | Cells/Cm$^2$ | | | Mean | Std. Dev. |
|---|---|---|---|---|---|---|
| | | Test 1 | | | | |
| Tris Buffer | — | 11508 | 11778 | | 11643 | ±135 |
| bIGF-II | 26 nM | 13401 | 12953 | | 13177 | ±224 |
| hIGF-I | 1 nM | 15519 | 15752 | | 15635 | ±116 |
| 2% FCS medium | — | 12313 | 12691 | | 12502 | ±189 |
| | | Test 2 | | | | |
| Tris Buffer | — | 8301 | | | — | — |
| bIGF-II | 52 nM | 10156 | | | — | — |
| hIGF-I | 1 nM | 10869 | 11004 | 10731 | 10868 | ±79 |
| 2% FCS medium | — | 8930 | 9676 | 9109 | 9252 | ±121 |

TABLE III

| Treatment | Conc.[a] | Test 3 Cells/cm$^2$ | | | Mean | Std. Dev. |
|---|---|---|---|---|---|---|
| Control A | — | 6391 | 6306 | 6039 | 6245 | 150 |
| bIGF-II | 500 nM | 11401 | 11223 | 10948 | 11191 | 186 |
| Control B | — | 6558 | — | — | 6558 | — |
| bIGF-II | 100 nM | 14037 | 13505 | 13905 | 13816 | 226 |
| Control C | — | 8138 | 8383 | 8276 | 8266 | 100 |
| bIGF-II | 50 nM | 12374 | 11781 | 12488 | 12214 | 310 |
| Control D | — | 9596 | 8836 | 8338 | 8923 | 517 |
| bIGF-II | 10 nM | 12175 | 11630 | 11348 | 11718 | 343 |
| bIGF-II | 5 nM | 11414 | 11239 | 10871 | 11175 | 226 |
| bIGF-II | 1 nM | 9916 | 9380 | 9420 | 9572 | 244 |
| bIGF-II | 0.5 nM | 8739 | 9135 | 9030 | 8968 | 167 |
| bIGF-II | 0.1 nM | 8754 | 8885 | 8697 | 8779 | 79 |
| hIGF-I | 1 nM | 11419 | 10653 | 10857 | 10976 | 324 |
| | 10 nM | 13676 | 13335 | 13926 | 13646 | 242 |

[a]Estimated by radioimmunoassay or area under HPLC peak.

EXAMPLE III

This example demonstrates the ability of bIGF-II to stimulate bovine mammary epithelial cell proliferation. Specifically, bIGF-II purified as in Example I was tested in a collagen gel culture system for its ability to stimulate such proliferation.

Mammary tissue from a 150–200 day pregnant, non-lactating Holstein cow was obtained at slaughter. Tissue was minced and placed in a 500 ml fluted Erlenmeyer flask containing 0.15% (w/v) collagenase (Batch #103-586; Boehringer Mannheim, Indianapolis, Ind.), 0.1% (w/v) hyaluronidase (Type 1, Sigma Chemical Co.), plus 5% (v/v) fetal bovine serum (FBS) in Medium 199 (both GIBCO). 90 ml of total solution was used per 5 gms of tissue. The dispersing solution was swirled on a gyrotory water bath at 60 rpm at 35° for 4–5 hours or until most clumps were dispersed. To remove large fragments, dispersed tissue, mixed with 0.02% (w/v) DNase, deoxyribonuclease I (Sigma Chemical Co.) was filtered through Nitex cloth (mesh size 153 µm, Tetko Co., Elmsford, N.Y.). Undigested clumps were collected and resuspended in 0.05% (w/v) pronase (Calbiochem-Behring Corp., LaJolla, Calif.) and swirled at 40 rpm at 35° for an additional 15 min. Mammary tissue was again filtered, collected by centrifugation, washed with Medium 199 and held on ice until density gradient separation.

Following enzyme dissociation, mammary fragments were resuspended in 1 ml of 0.02% DNase and layered on a preformed gradient of Percoll (Pharmacia Fine Chemicals, Piscataway, N.J.), as described in Richards et al. Briefly, 30 ml of 42% Percoll were centrifuged at 20,000×g for 1 hour to generate a continuous gradient.

Approximately $3 \times 10^7$ cells were layered on top of this gradient and centrifuged for 10 min at $800 \times g$. Epithelial organoids were collected from the 1.065–1.070 g/ml region of the gradient. Cell number estimates prior to culture were made by mixing one volume of cell suspension with nine volumes of 0.2% (v/v) crystal violet in 0.1 M citric acid. Stained nuclei were counted on a hemocytometer.

Basic techniques for the collagen gel culture system are described in Yang and Nandi. Collagen gel was prepared as described in Michalopoulos et al. with slight modification (Richards et al.). Briefly, 4 g sterilized rat tail collagen fibers (predominantly Type 1) were dissolved in 1 liter of sterile 0.017 M acetic acid at 4° for 48 hours. After centrifugation at $10,000 \times g$ for 60 min, the supernatant was collected and this served as the stock collagen solution. Each batch of collagen was individually titrated to pH 7.4, using solutions of 10X Medium 199 (no bicarbonate) (GIBCO) and 0.34 N NaOH in a ratio of 2:1.

For culturing cells within the collagen matrix, the neutralized collagen mixture was kept on ice to prevent gelation. Epithelial organoids in a minimal volume (0.5 ml) of Medium 199 were added yielding a final concentration of $4-6 \times 10^5$ cells/ml gelation mixture. The collagen-cell suspension (0.5 ml) was overlaid on 0.3 ml of pregelled collagen in each well of a 24 well plate (Costar, Cambridge, Mass.) and allowed to gel at room temperature. After this layer gelled, cultures were fed with 0.5 ml of a 1:1 mixture of Dulbecco's Modified Eagle's (DME):Hams F-12 (DME/F-12) (GIBCO) plus 3% (v/v) FBS, 10 ng/ml mouse epidermal growth factor (EGF) (Collaborative Research, Inc., Waltham, Mass.), antibiotics (GIBCO), and the appropriate test growth factor. Cultures were incubated at 37° in 95% air-5% $CO_2$ and the culture medium was changed every other day.

As shown in TABLE IV, the ability of bIGF-II to stimulate bovine mammary epithelial cell proliferation in the collagen gel assay system was tested in triplicate over a broad concentration range. A negative proliferation control, Basal Medium [DME/F-12+3% (w/v) FCS +EGF (10 ng/ml)], and positive proliferation controls, containing insulin at various supraphysiological concentrations, were simultaneously run. As shown in TABLE IV, bIGF-II stimulated bovine mammary epithelial cell proliferation at a statistically significant level at concentrations ranging from about 30 nM to about 100 nM.

contained 33.6 μl of bIGF-II solution+11.1 ml Basal Media (final conc. bIGF-II =500 nM). Stock solution 2 contained 6.7 μl of bIGF-II solution+11.1 ml Basal Media (final conc. bIGF-II=100 nm). Serial dilutions were made from these stocks and tested over a concentration range of 0.1 nM to 100 nM. Control media consisted of Basal Medium plus a corresponding volume of acetic acid if necessary (an appropriate control was necessary when the growth factor addition lowered pH of the test media). All media was adjusted to neutral pH by addition of 10% NaOH.

TABLE 2

| IGF-II Conc. | Control[a] | Cell Numbers/Well ($\times 10^4$) | | | Mean | Std. Dev. | % Increase Over Control |
|---|---|---|---|---|---|---|---|
| 100 nM | 2 | 37.9 | 43 | 34.8 | 38.6 | 4.1 | 94.0% |
| 50 nM | 3 | 35.9 | 38.9 | 37.9 | 37.5 | 1.5 | 76.1% |
| 10 nM | 1 | 33.8 | 39.9 | 38.9 | 37.5 | 3.3 | 30.6% |
| 5 nM | 1 | 34.8 | 29.8 | 39.9 | 34.8 | 5.1 | 21.2% |
| 1 nM | 1 | 33.8 | 33.8 | 35.9 | 34.5 | 1.2 | 20.2% |
| .5 nM | 1 | 22.7 | 25.7 | 30.8 | 26.4 | 4.1 | — |
| 0.1 nM | 1 | 26.7 | 29.8 | — | 28.2 | 2.1 | — |
| Controls | | | | | | | |
| 1 | | 29.8 | 31.8 | 24.7 | 28.7 | 3.7 | — |
| 2 | | 21.6 | 18.6 | 19.6 | 19.9 | 1.6 | — |
| 3 | | 19.6 | 24.7 | 19.6 | 21.3 | 2.9 | — |

[a]Appropriate Control
1 = Basal Medium
2 = Basal Medium + 33.6 μl 20% Acetic Acid; pH adjusted to 7.4 with 10% NaOH
3 = Basal Medium + 6.7 μl 20% Acetic Acid; pH adjusted to 7.4 with 10% NaOH

EXAMPLE 4

Restriction and DNA modifying enzymes used in the procedures described herein were from New England Biolabs (Beverly, Mass.). Except as specifically noted, the cloning and sequencing steps employed standard molecular biology procedures as described and/or referenced in Maniatis et al. (Maniatis).

Genomic DNA was isolated from calf kidney as described in Maniatis, pp. 280–281. The DNA probes used in the genomic Southern analysis and screening of the bovine genomic library described below were isolated as follows: A human IGF-II cDNA clone structurally of a kind published by Bell et al. and Dull et al. was obtained as a 1.7 kilobase pair (kbp) Eco RI fragment containing the cDNA diagrammed in FIG. 1, and cloned into the plasmid vector pUC18. The insert DNA was purified away from vector sequences by digestion with the restriction enzyme Eco RI followed by size-fractionation via electrophoresis through 0.7% w/v agarose (Maniatis, pp. 150–161). The DNA was stained with ethidium bromide (1 μg/ml), visualized under long-wave UV light, and the 1.7 kbp band was excised.

TABLE IV

| Treatment | Conc. | Test 1 Cell Numbers/Well ($\times 10^4$) | | | Mean | Std. Dev. | % Increase Over Control |
|---|---|---|---|---|---|---|---|
| bIGF-II | 0.1 nM | 29.5 | 28.8 | 19.9 | 26.1 | 5.4 | — |
| | 1.0 nM | 30.1 | 24.4 | 29.4 | 27.9 | 3.1 | — |
| | 3.3 nM | 29.0 | 22.4 | 18.6 | 23.3 | 5.3 | — |
| | 10.0 nM | 35.6 | 41.3 | 38.4 | 38.4 | 2.9 | 30.2 |
| | 33.0 nM | 42.2 | 46.4 | — | 44.3 | 2.9 | 50.2 |
| | 100.0 nM | 57.8 | 57.1 | 58.7 | 57.8 | 0.8 | 95.9 |
| Insulin | 17.0 nM | 31.5 | 35.9 | 34.7 | 34.1 | 2.3 | 15.6 |
| | 170.0 nM | 51.2 | 45.4 | 57.4 | 51.4 | 6.0 | 74.2 |
| | 1700.0 nM | 38.7 | 56.9 | 68.5 | 54.7 | 15.0 | 85.4 |
| Control[a] | | 29.4 | 29.7 | — | 29.5 | 0.25 | — |

[a]Basal Medium

In Test 2, peak HPLC material from Example I was dissolved in 20% acetic acid to an estimated concentration of 165 μM and added directly to the same Basal Medium to form two stock solutions. Stock solution 1

DNA was recovered by electroelution (Maniatis, p. 164) and further purified over elutip columns (Schleicher and Schuell, Keene, N.H.) according to the supplier's recommendations. This 1.7 kbp fragment was digested further with the restriction enzyme Rsa I to obtain the fragments diagrammed in FIG. 1. Each of these fragments was purified as described above for the 1.7 kbp fragment (Maniatis, pp. 150-164).

The 340 and 515 bp fragments, believed to include the entire coding sequence for the human IGF-II prepeptide, were used in the genomic Southern analysis and screening of a bovine genomic library described below.

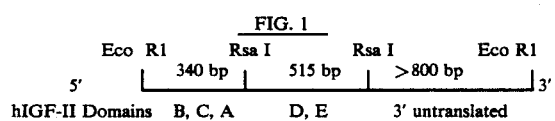

FIG. 1

From the A and B regions of hIGF-II shown in Dull et al., there were designed two synthetic oligomers which are herein designated IGF-IIA and IGF-IIB, respectively, and shown in FIG. 2.

DNA and tRNA were denatured by boiling for 10 minutes.

Probes were radiolabelled by nick translation (Maniatis, p. 109) to a specific activity of $10^7-10^8$ dpm/μg. Between 10; and $3\times10^8$ dpm of the appropriate nick-translated probe was added to the prehybridization mixture, which was then incubated for 48 hours at 42°. The filters were washed twice for 15 min at 42° in 1X SSPE/0.1% SDS, followed by a final wash (10–15 min) at the same temperature in 0.1X SSPE/0.1% SDS. The filters were air dried, and exposed to Kodak XAR film at $-70°$ for 2-3 days with one intensifying screen.

Results of a bovine genomic Southern analysis carried out with the 340 bp and 515 bp nick-translated probes (FIG. 1) are in TABLE V.

TABLE V

| Length of Band (kbp) | 340 bp Probe | 515 bp Probe |
|---|---|---|
| Eco RI | 4.4 | 4.4 |
| BAM HI | 6.0 | 8.2 |
| HIND III | 13.5 | 13.5 |

The length of each hybridizing band was determined by measuring the distance of the band from the top of

FIG. 2

IGF-IIA

| | 48 | 49 | 50 | 51 | 52 | 53 | 54 | 55 | 56 | 57 | 58 | |
|---|---|---|---|---|---|---|---|---|---|---|---|---|
| AA | Phe | Arg | Ser | Cys | Asp | Leu | Ala | Leu | Leu | Glu | Thr | |
| human 5' | TTC | CGC | AGC | TGT | GAC | CTG | GCC | CTC | CTG | GAG | ACG | 3' |
| probe 3' | AAG | GCG | TCG | ACA | CTG | GAC | CGG | GAG | GAC | CTC | TG | 5' |

IGF-IIB

| | 1 | 2 | 3 | 4 | 5 | 6 | 7 | 8 | 9 | 10 | 11 | 12 |
|---|---|---|---|---|---|---|---|---|---|---|---|---|
| AA | Ala | Tyr | Arg | Pro | Ser | Glu | Thr | Leu | Cys | Gly | Gly | Glu |
| human 5' | GCT | TAC | CGC | CCC | AGT | GAG | ACC | CTG | TGC | GGC | GGG | GAG 3' |
| probe 3' | CGA | ATG | GCG | GGG | TCA | CTC | TGG | GAC | ACG | CCG | CCC | C 5' |

These oligomers were synthesized on an Applied Biosystems, Inc. (Foster City, Calif.) DNA synthesizer Model 380 A or B. The oligomers were used to identify small subclones of the genomic clone which contained exon sequences, and in the case of IGF-IIB, as a primer for DNA sequencing.

Genomic blots of bovine kidney DNA were done using a modification of the method of Southern. In that modification, 20 μg bovine kidney DNA was digested with Eco R1, Bam HI or Hind III, fractionated on a 20×13.5 cm 0.7% (w/v) agarose gel, stained with ethidium bromide (1 μg/ml) and photographed. The DNA was denatured for two hours at 37° in 0.5 N NaOH/1.5 M NaCl, neutralized for an additional two hours at 37° in 0.5 M Tris-HCl(pH 8)/1.5 M NaCl, and transferred overnight onto Schleicher and Schuell nitrocellulose filters in 10X SSPE (1X SSPE is 180 mM NaCl, 10 mM sodium phosphate, pH 6.8, 1 mM EDTA, all from Sigma Chemical Co.). A sponge was used instead of a paper wick. The filters were washed briefly in 10X SSPE, air-dried, baked for 2-3 hours at 80° in a vacuum oven and soaked for one hour at 50° in 5X SSPE. Denhardt's was added to a final concentration of 5X (1X Denhardt's is 0.02% w/v bovine serum albumin, 0.02% Ficoll, 0.02% polyvinyl pyrrolidone, all from Sigma Chemical Co.) and the filters were soaked an additional hour.

The blots were prehybridized overnight at 37° in 25 ml of a mixture containing 50% (v/v) formamide; 5X SSPE; 5X Denhardt's; 0.1% (w/v) SDS (sodium dodecyl sulfate); and 100 μg/ml each of carrier salmon testes (ST) DNA and yeast tRNA. Prior to addition, the ST the gel compared to standard DNA's of known length electrophoresed on the same gel. Results indicated that the entire coding sequence of bIGF-II could be found on a 4.4 kbp Eco RI fragment. A genomic library containing Eco RI fragments of approximately this size was constructed as follows: Bovine kidney DNA was digested to completion with Eco RI and size-fractionated by electrophoresis through agarose as described above. DNA fragments 3.8 kbp to 4.8 kbp in length were excised from the gel and purified by electroelution (Maniatis, p. 164) followed by elutip column chromatography (Schleicher and Schuell). 100 nanograms of this size-selected DNA was ligated into the vector lambda gt10 from Vector Cloning Systems (San Diego, Calif.). This vector is used to clone Eco RI cut DNA fragments ranging in size between zero and seven kbp. It was obtained pre-cut with Eco RI and ready to be ligated. Ligation was carried out using standard conditions (Maniatis, p. 286). The resulting ligated DNA was packaged in vitro using Vector Cloning Systems packaging extracts. The titer of the library obtained was $1.5\times10^7$ plaque forming units (pfu) per μg of DNA ligated.

Screening of the library was carried out as follows: $1.2\times10^5$ pfu were plated on C600 cells as described in Maniatis, p. 320. The phage were plated at a density of 4000 pfu per 100 cm$^2$ plate containing NZC Agar (NZC is 10% w/v NZ amine, 0.5% w/v NaCl, 0.2% w/v MgCl$_2$ and 0.1% w/v casamino amino acids, all from Sigma Chemical Co.). Plates were incubated overnight at 37°, chilled at 4° for several hours, and transferred to nitrocellulose as described in Maniatis, p. 320. Hybridization to the nick-translated 340 bp and 515 bp probes was carried out as described above for Southern genomic blots.

Positive clones were selected and subjected to a second round of screening identical to the first round, with the exception that the phage density was reduced to 100–200 pfu/100 cm² plate. Positive clones from the second screen were plated out a third time as described, except that the phage density was reduced further to 20–50 pfu/100 cm² plate. Well-isolated positive clones from the third round of screening were picked and purified DNA was prepared from these plaques according to Maniatis, p. 76. The inserts were released from the lambda gt10 arms by Eco RI digestion and subcloned into pUC18 (New England Biolabs), to provide a convenient source of large amounts of the insert DNA. Plasmid DNA was prepared as described in Maniatis, p. 90.

To prepare fragments of DNA containing exon sequences which were of a convenient length for DNA sequencing (less than 500 bp) the following procedure was employed: The insert DNA was digested with the restriction endonucleases Alu 1, Hae III, Pst I or Sau 3A. These digestions produce random DNA fragments of sequenceable length. Each digest was ligated at random into the sequencing vectors M13mp18 and M13mp19 from New England Biolabs. The resulting plaques, obtained after transformation into JM101 cells (Maniatis, p. 250, and Messing et al.) were screened by hybridization to either the IGF-IIA or IGF-IIB oligomers to identify the desired clones containing exon sequences.

For these hybridizations the synthetic oligomers were end-labelled as described in Maniatis, p. 122. The prehybridization buffer was altered to exclude the formamide, and the concentrations of SSPE and Denhardt's were increased to 6X and 10X, respectively, as in Meinkoth et al. Hybridization was carried out at 30°–37° and the washing temperature was reduced to 37°. Filters were washed for shorter times (5–10 minutes) in 6X SSPE/0.1% SDS. DNA was prepared from plaques hybridizing to either probe as in Messing et al. The purified, single-stranded DNA was sequenced using the dideoxy technique described in Sanger et al, except that sulfur-35 labelled nucleotides (Amersham Corp., Arlington Heights, Ill.) were used in place of the P-32 nucleotides described in Sanger et al.

Exon/intron junctions were identified using three criteria: Open reading frames, exon/intron junction sequences and analogy to the human cDNA sequence. In the following sequences, the identified exon/intron junctions are shown by underlining the two (adjacent) nucleotides on either side of each junction.

By such sequencing, the nucleotide sequence coding for the mature bIGF-II peptide was found to be:

5'-GCT TAC CGC CCC AGC GAG ACT CTG TGC GGC
GGG GAG CTG GTG GAC ACC CTC CAG TTT GTC
TGT GGG GAC CGC GGC TTC TAC TTC A<u>GC</u> CGA
CCA TCC AGC CGC ATA AAC CGA CGC AGC CGT
GGC ATC GTG GAA GAG TGT TGC TTC CGA AGC
TGC GAC CTG GCC CTG CTG GAG ACT TAC TGT
GCC ACC CCC GCC AAG TCC GAG-3'.

Also determined by the foregoing procedure was the following DNA sequence coding for bIGF-II linked directly at its amino end to a leader of 24 additional amino acids:

5'-ATG GGA ATC CCA ATG GGG AAG TCG ATG CTG
GTG CTT CTC ACC TTC CTT GCC TTC GCC TCG
TGC TGC ATT GCT GCT TAC CGC CCC AGC GAG
ACT CTG TGC GGC GGG GAG CTG GTG GAC ACC
CTC CAG TTT GTC TGT GGG GAC CGC GGC TTC
TAC TTC AGC CGA CCA TCC AGC CGC ATA AAC
CGA CGC A<u>GC</u> CGT GGC ATC GTG GAA GAG TGT
TGC TTC CGA AGC TGC GAC CTG GCC CTG CTG
GAG ACT TAC TGT GCC ACC CCC GCC AAG TCC
GAG-3'.

Another sequence determined by the foregoing procedure was that of the following DNA coding for mature bIGF-II linked directly at its carboxy end to an extension of 68 amino acids.

5'-GCT TAC CGC CCC AGC GAG ACT CTG TGC GGC
GGG GAG CTG GTG GAC ACC CTC CAG TTT GTC
TGT GGG GAC CGC GGC TTC TAC TTC A<u>GC</u> CGA
CCA TCC AGC CGC ATA AAC CGA CGC AGC CGT
GGC ATC GTG GAA GAG TGT TGC TTC CGA AGC
TGC GAC CTG GCC CTG CTG GAG ACT TAC TGT
GCC ACC CCC GCC AAG TCC GAG AGG GAT GTG
TCT GCC TCT ACG ACC GTG CTT CC<u>G GA</u>C GAC
GTC ACC GCA TAC CCC GTG GGC AAG TTC TTC
CAA TAT GAC ATC TGG AAG CAG TCC ACC CAG
CGC CTG CGC AGG GGC CTG CCC GCC TTC CTG
CGA GCA CGC CGG GGT CGC ACG CTC GCC AAG
GAG CTG GAG GCG CTC AGA GAG GCC AAG AGT
CAC CAT CCG CTG ATC-3'.

By the foregoing procedure, there was also determined the following nucleotide sequence of DNA coding for a bIGF-II precursor including the aforedescribed N-terminal leader and C-terminal extension:

5'-ATG GGA ATC CCA ATG GGG AAG TCG ATG CTG
GTG CTT CTC ACC TTC CTT GCC TTC GCC TCG
TGC TGC ATT GCT GCT TAC CGC CCC AGC GAG
ACT CTG TGC GGC GGG GAG CTG GTG GAC ACC
CTC CAG TTT GTC TGT GGG GAC CGC GGC TTC
TAC TTC A<u>GC</u> CGA CCA TCC AGC CGC ATA AAC
CGA CGC AGC CGT GGC ATC GTG GAA GAG TGT
TGC TTC CGA AGC TGC GAC CTG GCC CTG CTG
GAG ACT TAC TGT GCC ACC CCC GCC AAG TCC
GAG AGG GAT GTG TCT GCC TCT ACG ACC GTG
CTT CC<u>G GA</u>C GAC GTC ACC GCA TAC CCC GTG
GGC AAG TTC TTC CAA TAT GAC ATC TGG AAG
CAG TCC ACC CAG CGC CTG CGC AGG GGC CTG
CCC GCC TTC CTG CGA GCA CGC CGG GGT CGC
ACG CTC GCC AAG GAG CTG GAG GCG CTC AGA
GAG GCC AAG AGT CAC CAT CCG CTG ATC-3'.

The bIGF-II peptides produced by expression of the immediately preceding three nucleotide sequences have substantially the biological activity of bIGF-II (in general, after removal of the aforementioned leader sequence from those peptides containing same and/or suitable naturation, as required) and can be used instead of the shorter (e.g. 67 AA) peptides of this invention (in some cases advantageously) to provide biological effects like those of bIGF-II in animals.

Cited Publications

1. Bala, R. M. and Bhaumick, B. (1979) *Can. J. Biochem.* 57:1289-98
2. Bell, G. I., Merryweather, J. P., Sanchez-Pescador, R., Stempien, M. M., Priestley, L., Scott, J. and Rall, L. B. (1984) *Nature* 310:775-77
3. Daughaday, W. H. et al. (1981) *J. Clin. Endocrinol. & Metab.* 53:282-88
4. Dull, T. J., Gray, A., Hayflick, J. S., and Ullrich, A. (1984) *Nature* 310:777-81
5. Gospodarowicz, D., Weseman, J., Moran, J. S. and Lindstrom, J. (1976) *J. Cell Biol.* 70:395-405
6. Hirs, C. H. W. (1956) *J. Biol. Chem.* 219:611-621
7. Humbel, R. E. (1984) in *Hormonal Proteins and Peptides*, ed. Choh Hao Li, Academic Press, Inc., XII:66-68
8. Hunkapiller et al. (1983a) *Methods in Enzymol.*, C. H. W. Hirs et al., Eds. (Academic Press, New York, N.Y.) 91:399-413
9. Hunkapiller et al. (1983b) Methods in Enzymol., C. H. W. Hirs et al., Eds. (Academic Press, New York, N.Y.) 91:486-493
10. Kotts, C. E. (1984) *Ph.D. Dissertation*, Univ. of Minnesota, St. Paul, Minn.
11. Kotts, C. E. and Baile, C. A. (1985) *Fed Proc.* 44(3):484
12. Larsen, B. R. and West, F. G. (1981) *J. Chromato. Sci.* 19:259-65
13. Lehninger, A. L. (1976) *Biochemistry*, 2nd Ed., Worth Publishers, Inc. New York, N.Y., pp. 72-75, 315-322
14. Liberti (1975) *Biochem & Biophys. Res. Comm.* 67:1226-1233
15. Maniatis, T., Fritsch, E. F. and Sambrook, J. (1982) in *Molecular Cloning: A Laboratory Manual* (Cold Springs Harbor Laboratory, Cold Springs Harbor, N.Y.)
16. Marquardt, H. et al. (1981) *J. Biol. Chem.* 256:6859-63
17. Meinkoth, J. and Wahl, G. (1984) *Anal. Biochemistry* 138:267-84
18. Messing, J., Crea, R. and Seeburg, P. H. (1981) *Nucl. Acids Res.* 9:4173-88
19. Michalapoulos, G. and Pitot, H. C. (1975) *Exp. Cell Res.* 94:70-78
20. Richards et al. (1983) *J. Tissue Cult. Methods* 8:31-39
21. Rinderknecht and Humbel, E. E. (1978) *FEBS Letters* 89:283-86
22. Sanger, F., Nicklen, S. and Coulson, A. R. (1977) *Proc. Natl. Acad. Sci. USA* 74:5463-67
23. Southern, E. M. (1975) *J. Mol. Biol.* 98:503-17
24. Strain, A J., Hill, D. J., Swenne, I., and Milner, R. D. G. (1986) *British Endocrine Society Abstracts*, Abs #142
25. Svoboda et al. (1980) *Biochemistry* 19:790-97
26. Van Wyk, J. J. et al. (1975) *Adv. Metab. Disorders* 8:127-50
27. Woo, S. L. C. (1979) *Methods in Enzymol.*, R. Wu, Ed. (Academic Press, New York) 68:389-95
28. Yaffee, D. (1968) *Proc. Nat'l. Acad Sci., U.S.A.* 61:477
29. Yang, J. and Nandi, S. (1983) *Int. Rev. of Cytol.* 81:249-86
30. Yamashiro, D., and Li, C. H. (1985) *Int. J. Peptide Protein Res.* 26:299-304
31. Zumstein, P. P. and Humbel, R. E. (1985) *Methods in Enzymology*, L. Bimbaumer et al., Eds. (Academic Press, New York, N.Y.) 109:782-98

What is claimed is:

1. Essentially pure DNA containing a sequence of nucleotides coding for a synthetic peptide consisting essentially of the following sequence of amino acids, reading from the amino end to the carboxy end of said sequence:

Ala—Tyr—Arg—Pro—Ser—Glu—Thr—Leu—Cys—Gly—
Gly—Glu—Leu—Val—Asp—Thr—Leu—Gln—Phe—Val—
Cys—Gly—Asp—Arg—Gly—Phe—Tyr—Phe—Ser—Arg—
Pro—Ser—Ser—Arg—Ile—Asn—Arg—Arg—Ser—Arg—
Gly—Ile—Val—Glu—Glu—Cys—Cys—Phe—Arg—Ser—
Cys—Asp—Leu—Ala—Leu—Leu—Glu—Thr—Tyr—Cys—
Ala—Thr—Pro—Ala—Lys—Ser—Glu

2. Synthetic DNA containing a sequence of nucleotides coding for a peptide of claim 1.

3. DNA of claim 2 containing the following sequence of nucleotides or their functional equivalents for expression of said peptide:

5'-GCT TAC CGC CCC AGC GAG ACT CTG TGC GGC
GGG GAG CTG GTG GAC ACC CTC CAG TTT GTC
TGT GGG GAC CGC GGC TTC TAC TTC AGC CGA
CCA TCC AGC CGC ATA AAC CGA CGC AGC CGT
GGC ATC GTG GAA GAG TGT TGC TTC CGA AGC
TGC GAC CTG GCC CTG CTG GAG ACT TAC TGT
GCC ACC CCC GCC AAG TCC GAG-3'.

4. Synthetic DNA containing a sequence of nucleotides coding for a peptide of claim 1 linked directly at its amino end to the carboxy terminus of the following sequence of amino acids:

Met—Gly—Ile—Pro—Met—Gly—Lys—Ser—Met—Leu—
Val—Leu—Leu—Thr—Phe—Leu—Ala—Phe—Ala—Ser—
Cys—Cys—Ile—Ala— or a portion thereof.

5. DNA of claim 4 containing the following sequence of nucleotides or their functional equivalents for expression of such a peptide:

5'-ATG GGA ATC CCA ATG GGG AAG TCG ATG CTG
GTG CTT CTC ACC TTC CTT GCC TTC GCC TCG
TGC TGC ATT GCT GCT TAC CGC CCC AGC GAG
ACT CTG TGC GGC GGG GAG CTG GTG GAC ACC
CTC CAG TTT GTC TGT GGG GAC CGC GGC TTC
TAC TTC AGC CGA CCA TCC AGC CGC ATA AAC
CGA CGC AGC CGT GGC ATC GTG GAA GAG TGT
TGC TTC CGA AGC TGC GAC CTG GCC CTG CTG
GAG ACT TAC TGT GCC ACC CCC GCC AAG TCC
GAG-3'.

6. Synthetic DNA containing a sequence of nucleotides coding for a peptide of claim 1 linked directly at its carboxy end to the amino-terminus of the following sequence of amino acids:

—Arg—Asp—Val—Ser—Ala—Ser—Thr—Thr—Val—Leu
Pro—Asp—Asp—Val—Thr—Ala—Tyr—Pro—Val—Gly—
Lys—Phe—Phe—Gln—Tyr—Asp—Ile—Trp—Lys—Gln—
Ser—Thr—Gln—Arg—Leu—Arg—Arg—Gly—Leu—Pro—
Ala—Phe—Leu—Arg—Ala—Arg—Arg—Gly—Arg—Thr—
Leu—Ala—Lys—Glu—Leu—Glu—Ala—Leu—Arg—Glu—

-continued

Ala—Lys—Ser—His—His—Pro—Leu—Ile or a portion thereof.

7. DNA of claim 6 containing the following sequence of nucleotides or their functional equivalents for expression of such a peptide:

5'-GCT TAC CGC CCC AGC GAG ACT CTG TGC GGC
GGG GAG CTG GTG GAC ACC CTC CAG TTT GTC
TGT GGG GAC CGC GGC TTC TAC TTC AGC CGA
CCA TCC AGC CGC ATA AAC CGA CGC AGC CGT
GGC ATC GTG GAA GAG TGT TGC TTC CGA AGC
TGC GAC CTG GCC CTG CTG GAG ACT TAC TGT
GCC ACC CCC GCC AAG TCC GAG AGG GAT GTG
TCT GCC TCT ACG ACC GTG CTT CCG GAC GAC
GTC ACC GCA TAC CCC GTG GGC AAG TTC TTC
CAA TAT GAC ATC TGG AAG CAG TCC ACC CAG
CGC CTG CGC AGG GGC CTG CCC GCC TTC CTG
CGA GCA CGC CGG GGT CGC ACG CTC GCC AAG
GAG CTG GAG GCG CTC AGA GAG GCC AGG AGT
CAC CAT CCG CTG ATC-3'.

8. Synthetic DNA containing a sequence of nucleotides coding for a peptide of claim 1 linked directly to additional amino acids as set forth in claims 4 and 6.

9. DNA of claim 8 containing the following sequence of nucleotides or their functional equivalents for expression of such a peptide:

5'-ATG GGA ATC CCA ATG GGG AAG TCG ATG CTG
GTG CTT CTC ACC TTC CTT GCC TTC GCC TCG
TGC TGC ATT GCT GCT TAC CGC CCC AGC GAG
ACT CTG TGC GGC GGG GAG CTG GTG GAC ACC
CTC CAG TTT GTC TGT GGG GAC CGC GGC TTC
TAC TTC AGC CGA CCA TCC AGC CGC ATA AAC
CGA CGC AGC CGT GGC ATC GTG GAA GAG TGT
TGC TTC CGA AGC TGC GAC CTG GCC CTG CTG
GAG ACT TAC TGT GCC ACC CCC GCC AAG TCC
GAG AGG GAT GTG TCT GCC TCT ACG ACC GTG
CTT CCG GAC GAC GTC ACC GCA TAC CCC GTG
GGC AAG TTC TTC CAA TAT GAC ATC TGG AAG
CAG TCC ACC CAG CGC CTG CGC AGG GGC CTG
CCC GCC TTC CTG CGA GCA CGC CGG GGT CGC
ACG CTC GCC AAG GAG CTG GAG GCG CTC AGA
GAG GCC AAG AGT CAC CAT CCG CTG ATC-3'.

* * * * *